(12) United States Patent
Lechmann et al.

(10) Patent No.: US 8,133,281 B2
(45) Date of Patent: Mar. 13, 2012

(54) INTERVERTEBRAL IMPLANT COMPRISING DOME-SHAPED JOINT SURFACES

(75) Inventors: Beat Lechmann, Bettlach (CH); Roger Bürki, Balsthal (CH); Robert Frigg, Bettlach (CH)

(73) Assignee: Synthes USA, LLC, West Chester, PA (US)

( * ) Notice: Subject to any disclaimer, the term of this patent is extended or adjusted under 35 U.S.C. 154(b) by 1041 days.

(21) Appl. No.: 11/338,454

(22) Filed: Jan. 23, 2006

(65) Prior Publication Data
US 2006/0229725 A1 Oct. 12, 2006

Related U.S. Application Data

(63) Continuation of application No. PCT/CH03/00495, filed on Jul. 22, 2003.

(51) Int. Cl.
*A61F 2/44* (2006.01)
(52) U.S. Cl. ........................ 623/17.14; 623/17.11
(58) Field of Classification Search .... 623/17.11–17.16; 606/279
See application file for complete search history.

(56) References Cited

U.S. PATENT DOCUMENTS

| | | | |
|---|---|---|---|
| 3,658,056 A | 4/1972 | Huggler et al. | |
| 5,169,597 A * | 12/1992 | Davidson et al. | 428/613 |
| 5,314,477 A | 5/1994 | Marnay | 623/17 |
| 5,556,431 A | 9/1996 | Büttner-Janz | |
| 5,662,158 A | 9/1997 | Caldarise | |
| 5,879,407 A | 3/1999 | Waggener | |
| 5,893,889 A * | 4/1999 | Harrington | 623/17.16 |
| 5,895,428 A | 4/1999 | Berry | |
| 5,899,941 A * | 5/1999 | Nishijima et al. | 623/17.15 |
| 6,375,682 B1 * | 4/2002 | Fleischmann et al. | 623/17.12 |
| 6,514,289 B1 | 2/2003 | Pope et al. | 623/23.6 |
| 6,517,580 B1 * | 2/2003 | Ramadan et al. | 623/17.15 |

(Continued)

FOREIGN PATENT DOCUMENTS

CN 2288707 Y 8/1998

(Continued)

OTHER PUBLICATIONS

Notice of the Reason for the Rejection issued by the Japanese Patent Office dated Nov. 19, 2008.

(Continued)

*Primary Examiner* — Thomas C. Barrett
*Assistant Examiner* — Matthew Lawson
(74) *Attorney, Agent, or Firm* — McKeon, Meunier, Carlin & Curfman, LLC

(57) ABSTRACT

An intervertebral implant with a central axis, a top part, a bottom part, a joint comprising a joint part and a joint shell, and a joining means. The top part has a top apposed surface that is suitable for placing it on a vertebra situated above it; The bottom part has a bottom apposed surface, that is suitable for placing it on a vertebra situated below it. One of the two parts is operatively associated with a convex joint part and the other part to a matching joint shell. The joint part and the joint shell are mounted against one another in a sliding manner such that the top part and the bottom part can rotate relative to one another at least about one axis of rotation. The joining means holds the top part and the bottom part together without impairing the capability of the joint to pivot while allowing a clearance between the joint part and the joint shell.

9 Claims, 4 Drawing Sheets

U.S. PATENT DOCUMENTS

| | | | | |
|---|---|---|---|---|
| 6,673,113 | B2 * | 1/2004 | Ralph et al. | 623/17.13 |
| 7,001,433 | B2 * | 2/2006 | Songer et al. | 623/17.16 |
| 7,101,399 | B2 * | 9/2006 | Errico et al. | 623/17.14 |
| 7,179,294 | B2 * | 2/2007 | Eisermann et al. | 623/17.15 |
| 7,244,275 | B2 * | 7/2007 | Michelson | 623/23.5 |
| 7,267,691 | B2 * | 9/2007 | Keller et al. | 623/17.14 |
| 7,314,487 | B2 * | 1/2008 | Ralph et al. | 623/17.13 |
| 7,326,250 | B2 * | 2/2008 | Beaurain et al. | 623/17.14 |
| 7,442,211 | B2 * | 10/2008 | de Villiers et al. | 623/17.14 |
| 2003/0074073 | A1 * | 4/2003 | Errico et al. | 623/17.14 |
| 2003/0233146 | A1 * | 12/2003 | Grinberg et al. | 623/17.14 |
| 2004/0143332 | A1 * | 7/2004 | Krueger et al. | 623/17.14 |
| 2005/0021146 | A1 * | 1/2005 | de Villiers et al. | 623/17.15 |
| 2005/0159818 | A1 * | 7/2005 | Blain | 623/17.15 |
| 2006/0009850 | A1 * | 1/2006 | Frigg et al. | 623/17.13 |
| 2006/0122703 | A1 * | 6/2006 | Aebi et al. | 623/17.15 |
| 2008/0133011 | A1 * | 6/2008 | de Villiers et al. | 623/17.11 |
| 2008/0154383 | A1 | 6/2008 | Lechmann et al. | 623/18.11 |

FOREIGN PATENT DOCUMENTS

| | | | |
|---|---|---|---|
| DE | 100 37 504 | | 2/2002 |
| DE | 101 30 798 | | 7/2003 |
| EP | 1 374 807 | | 1/2004 |
| WO | WO 01/01893 | | 1/2001 |
| WO | WO 02/089701 | * | 11/2002 |

OTHER PUBLICATIONS

Chinese Office Action, issued on Apr. 24, 2009, for Chinese Patent Application No. 03826779.9.

U.S. Appl. No. 11/722,905, Non-Final Office Action, dated Jan. 16, 2009.

U.S. Appl. No. 11/722,905, Amendment in Response to the Non-Final Office Action Dated Jan. 16, 2009.

U.S. Appl. No. 11/722,905, Final Office Action, dated Sep. 29, 2009.

U.S. Appl. No. 11/722,905—Request for Continued Examination and Amendment in Response to the Final Office Action Dated Sep. 29, 2009.

* cited by examiner

INTERVERTEBRAL IMPLANT COMPRISING DOME-SHAPED JOINT SURFACES

CROSS-REFERENCE TO RELATED APPLICATION

This application is a continuation of International Patent Publication PCT/CH2003/000495, filed Jul. 22, 2003, which is incorporated by reference herein in its entirety.

FIELD OF THE INVENTION

The present invention relates to an intervertebral implant and, more particularly, to an artificial intervertebral implant.

BACKGROUND OF THE INVENTION

Intervertebral disks often become damaged creating discomfort for a patient. It is known that partial or total removal of a damaged intervertebral disk may alleviate some of this discomfort but may limit the natural function of the spine. Thus, nowadays following the removal of a damaged, natural intervertebral disk or a damaged nucleus pulposus of a natural intervertebral disk, an implant or prosthesis is placed in the intervertebral space between the two vertebra adjacent to the site of removal. The aim of implanting such devices is to bring about an as natural state as possible, particularly duplicating the original height of the intervertebral disk and consequently restoring the original distance between the two adjacent bodies of the vertebra. Furthermore, movements of adjacent bodies of the vertebra relative to one another should be able to be carried out with minimal hindrance of their natural function. For this purpose the retention of the ability to move when bending forward or backward, i.e. the flexion and the extension of the bodies of the vertebra as well as the lateral bending of the intervertebral bodies within the natural limits, is desirable. It is also desirable that the natural ligaments and muscles along the spine are left substantially intact, to further stabilize the movements of a mechanical replacement for a intervertebral disk.

Such an intervertebral implant is known from U.S. Pat. No. 5,556,431 to Büttner. This known implant comprises a bottom base plate and a top cover plate, the exterior surfaces of which can be placed on the adjacent bodies of the vertebra, as well as a joint provided between the cover plates. This joint consists of a hemispherical first joint part and a matching joint shell as the second joint part, so that the cover plates can pivot polyaxially relative to one another. A disadvantage of this known intervertebral implant is that although the two cover plates are connected with a joint part each, the joint parts are not held together. This requires the implant to be assembled by the surgeon creating a possibility for erroneous assembly. In-situ the joint parts and consequently the entire implant must be held together using a special instrument. This creates a possibility that the implant will fall apart prior to and during implantation, risking damage to surrounding tissue and risking loss of parts.

From U.S. Pat. No. 5,895,428 to Berry an intervertebral implant is known, that comprises joining means to hold the joint parts together. A disadvantage however, of this known intervertebral implant is that during a relative movement of the two joint parts the joining means slide on one another without any clearance and no lubricating film of the body's own fluids can be formed on them. A lubricating film of the body's own fluids may advantageously reduce wear and erosion between the sliding surfaces.

SUMMARY OF THE INVENTION

Thus it is desirable to produce a device for artificial replacement of an intervertebral disc, that has a joint that can execute a rotary movement, can be pre-assembled and where the joint parts can be held together with a clearance by joining means so that a lubricating film of the body's own fluids can form between the sliding joint surfaces. Further it would be desirable that such clearance be within a physiologically required range so as not to hinder the movement of the joint parts.

It would be further desirable that the joining means holding the parts together could be achieved using geometrically simple elements to reduce costs of manufacture. And still further it is desirable to have a joint with only a single pair of articular surfaces.

An intervertebral implant herein described includes a top part, a bottom part, a joint and a joining means. The top part comprises a top apposed surface suitable for placement against a vertebra situated above and adjacent the top part. The bottom part comprises a bottom apposed surface suitable for placement against a vertebra situated below and adjacent the bottom part. The joint preferably connects the top part and the bottom part and comprises a convex joint part with an articular surface and a joint shell with an articular surface. The joint part and the joint shell are mounted in a sliding manner. Either the top part or the bottom part is operatively associated with the convex joint part and the other part is operatively associated with the joint shell such that the top part and the bottom part can rotate relative to one another about at least one axis of rotation. The joining means preferably holds the top part and the bottom part together without impairing the capability of the joint to pivot and whilst permitting an axial clearance between the joint part and the joint shell.

In a further embodiment of the implant the joining means comprises an anchoring means that can be joined with the top part and is loosely mounted between the bottom part and the joint. The convex joint part may comprise a hollow space, that is open on the virtual apex of the convex joint part and in which the anchoring element can be axially displaced until it comes to a rest on the wall of the hollow space after overcoming a given axial clearance. The hollow space may be cylindrical. The hollow space may contract along the axis of rotation of the joint.

In another embodiment of the implant the convex joint part comprises a spherical first articular surface and the joint shell has a second articular surface, matching the first articular surface.

In a further embodiment of the implant, the convex joint part and the joint shell may be made from a metal/plastics material pair.

In another embodiment of the implant the articulating surfaces of the joint part and the joint shell are coated with some friction reducing substance.

In a further embodiment of the implant the top and bottom apposed surfaces are coated with titanium.

In another embodiment the top apposed surface and the bottom apposed surface are provided with macroscopic structures. The macroscopic structures may be protuberances. The protuberances may be pyramidal. Some protuberances may take the form of a wedge-shaped ridge or saw-tooth like serrations that are situated in a straight line. The protuberances may be coated at least partly with a coating of some substance that integrates with bone.

BRIEF DESCRIPTION OF THE DRAWINGS

The features of the invention will be better understood by reference to the accompanying drawings which illustrate presently preferred embodiments of the invention. It will nevertheless be understood that the invention should not be limited to such preferred embodiments and that the features may be used singularly or in combinations and that modification and alterations of the illustrated and described devices and methods are contemplated. In the drawings.

DETAILED DESCRIPTION OF THE INVENTION

Figure 1:
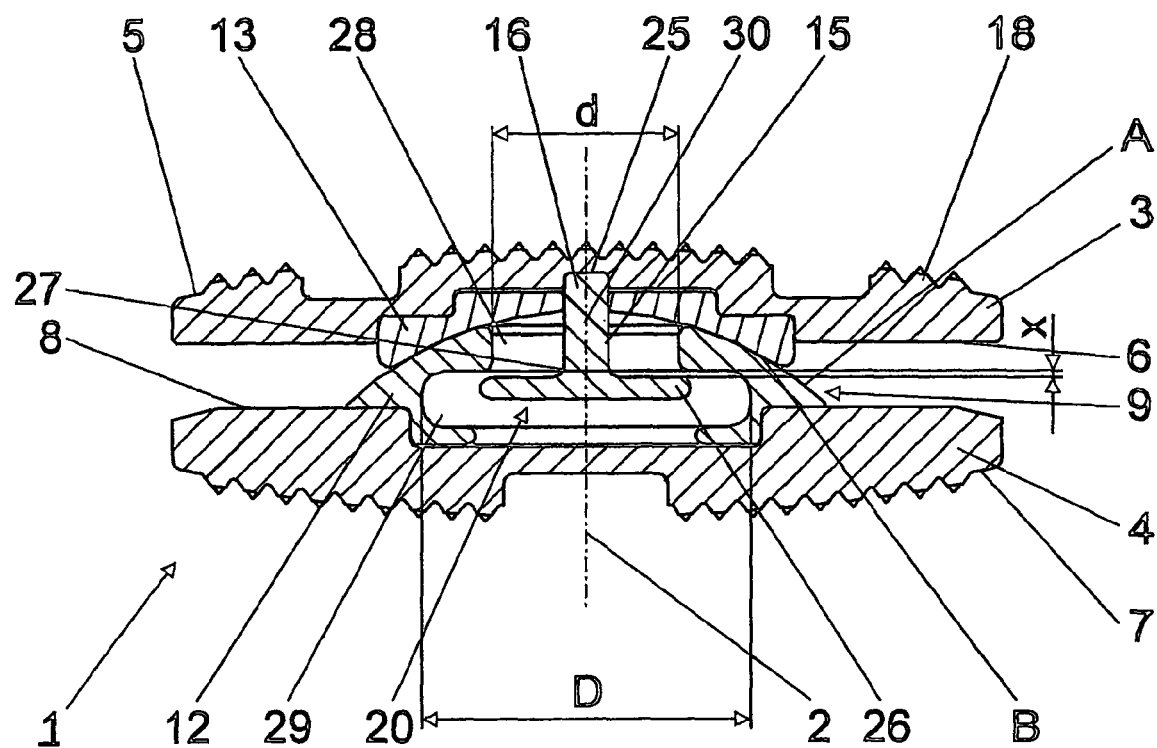
FIG. 1 is a section through an embodiment of the device of the present invention.
Figure 2:
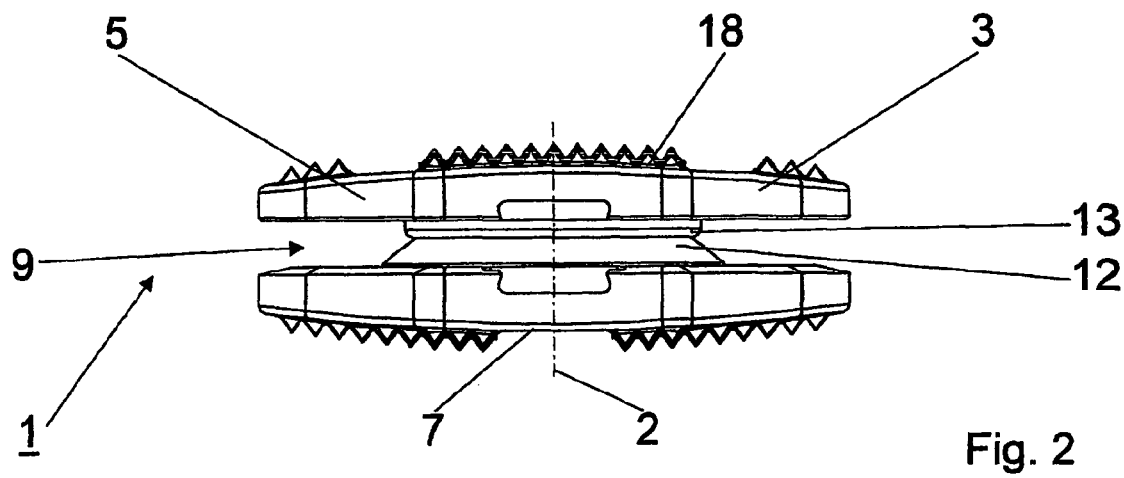
FIG. 2 is a dorsal view of the device of FIG. 1.
Figure 3:
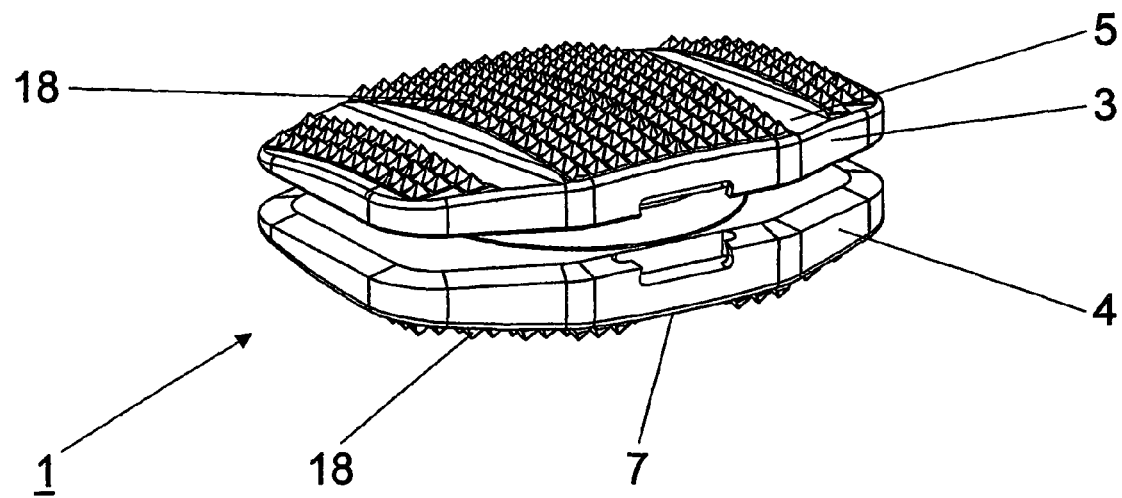
FIG. 3 is a perspective view of the device of FIGS. 1 and 2.

The embodiment of the intervertebral implant 1 illustrated in FIGS. 1-4 comprises a central axis, a top part 3, a bottom part 4, a joint 9 and an anchoring element 15. The top part 3 comprises a top apposed surface 5 that intersects a central axis 2 wherein the top apposed surface 5 is adapted to be placed adjacent and preferably in contact with a vertebra located above the site of a removed intervertebral disk. The bottom part 4 comprises a bottom apposed surface 7 that intersects a central axis 2 wherein the bottom apposed surface 7 is adapted to be placed adjacent and preferably in contact with a vertebra located above the site of a removed intervertebral disk. The joint 9 intersects the central axis and is provided between the top part 3 and bottom part 4, for the articulated joining of the top part 3 and bottom part 4. The joint 9 has a two-part construction comprising a convex joint part 12 and a joint shell 13. The convex joint part 12 is shaped as a partial spherical segment and comprises a second articular surface B. The convex joint part 12 is joined with the bottom part 4. The joint shell 13 matches the convex joint part 12 and has a first articular surface A. The joint shell 13 is preferably joined with the top part 3. By virtue of the partial spherical shape of the articular surfaces both parts can be pivoted polyaxially relative to one another. The anchoring element 15 holds the top part 3 and the bottom part 4 together and will be discussed in greater detail infra.

In one embodiment of the implant the top part 3 and bottom part 4 are coated with titanium on the apposed surfaces.

The top part 3 and the joint shell 13 are made of two parts in the embodiment illustrated in FIG. 1 so that the top part 3 and joint shell 13 can be manufactured, for example from a combination of materials. A range of metal/plastic combinations are known to those of skill in the art and provide the advantage of allowing relatively low friction sliding between the articular surfaces, damping of axial load impacts on the joint and being biocompatible and proven to perform as a joint implant. An exemplary pairing is titanium or a cobalt-chromium alloy top part 3 and a highly cross-linked polyethylene (X-UHMWPE) joint shell.

In another embodiment the articular surfaces A, B are coated with a substance that results in a reduced coefficient of friction between the articular surfaces A, B. Some exemplary substances include titanium carbide and amorphous carbon (ADLC) although other such substance will be known to one of skill in the art.

The dimensions of the articular surfaces depend upon the application. In a preferred embodiment the radius of the first articular surface A of the convex spherical joint part is between about 3 mm and about 25 mm, more preferably between about 4 mm and about 20 mm.

The convex joint part 12 is substantially concentric with the central axis 2 and converges towards the bottom surface 6 of the top part 3. The joint shell 13 is also substantially concentric with the central axis 2, while the opening of the joint shell 13 is directed towards the top surface 8 of the bottom part 4. The anchoring element 15, by which the two parts 3, 4 are held together, is substantially coaxial with the central axis 2 and comprises a pin 16, that with its slot end 25 passes through the joint shell 13 at approximately a virtual apex 30 on its surface and is fastened to the top part 3 and has a circular disc-shaped extension or plate 26 with a greater diameter, said extension provided on the front end 27 of the pin 16. The convex joint part 12 has an opening 28 that commences from its articular surface and is coaxial with the central axis 2 and terminates in a cylindrical hollow space 29 with a greater diameter in the interior of the convex joint part 12. The hollow space 29 is open approximately on the virtual apex 30 of the convex joint part 12 and is configured such that the anchoring element 15 can be axially displaced until it comes to rest on the wall of the hollow space 12 after overcoming the axial clearance X. Configuring joining means as illustrated may further result in low manufacturing costs. The geometry of the anchoring element 15, as well as of the opening 28 and that of the hollow space 29 is so chosen, that the pin 16 and the extension 26 in the opening 28 and in the hollow space 29, respectively, are arranged in a displaceable manner. The diameter of the opening 28 is smaller than the diameter of the disc-shaped plate 26, so that the convex joint part 12 and the joint shell 13 and consequently the two parts 3, 4 fastened on them, are axially held together without hindering the movement of the joint 9. The mobility of the pin 16 in the opening 28 and of the plate 26 in the hollow space 29 make a polyaxial pivoting of the two parts 3, 4 relative to one another possible. The length of the pin 16 is so dimensioned, that for any articulation of the joint 9 the extension 26 on the front end 27 of the pin 16 comes to a rest only after overcoming the clearance X at the transition between the opening 28 and the hollow space 29. In one embodiment the clearance X is at least about 0.005 mm, preferably at least about 0.05 mm. This will result in the advantage, that a lubricating film with the thickness X of the body's own fluids can be formed between the sliding surfaces. Furthermore, the articular surfaces can be protected from getting damaged by means of additional temporary fixing means.

In another embodiment, the clearance X is a maximum of about 0.5 mm and the cylindrical hollow space 29 has a diameter D between about 6 mm and about 20 mm, and a height H of the hollow space, measured parallel to the central axis between about 0.5 mm and about 8 mm.

In a further embodiment, the cylindrical hollow space 29 has a contraction that is coaxial with the central axis and terminates in the articular surface A of the convex joint part, the contraction is cylindrical and coaxial with the central axis, and the contraction has a diameter d, while the ratio of d:D is between about 30% and about 75%.

Figure 4:
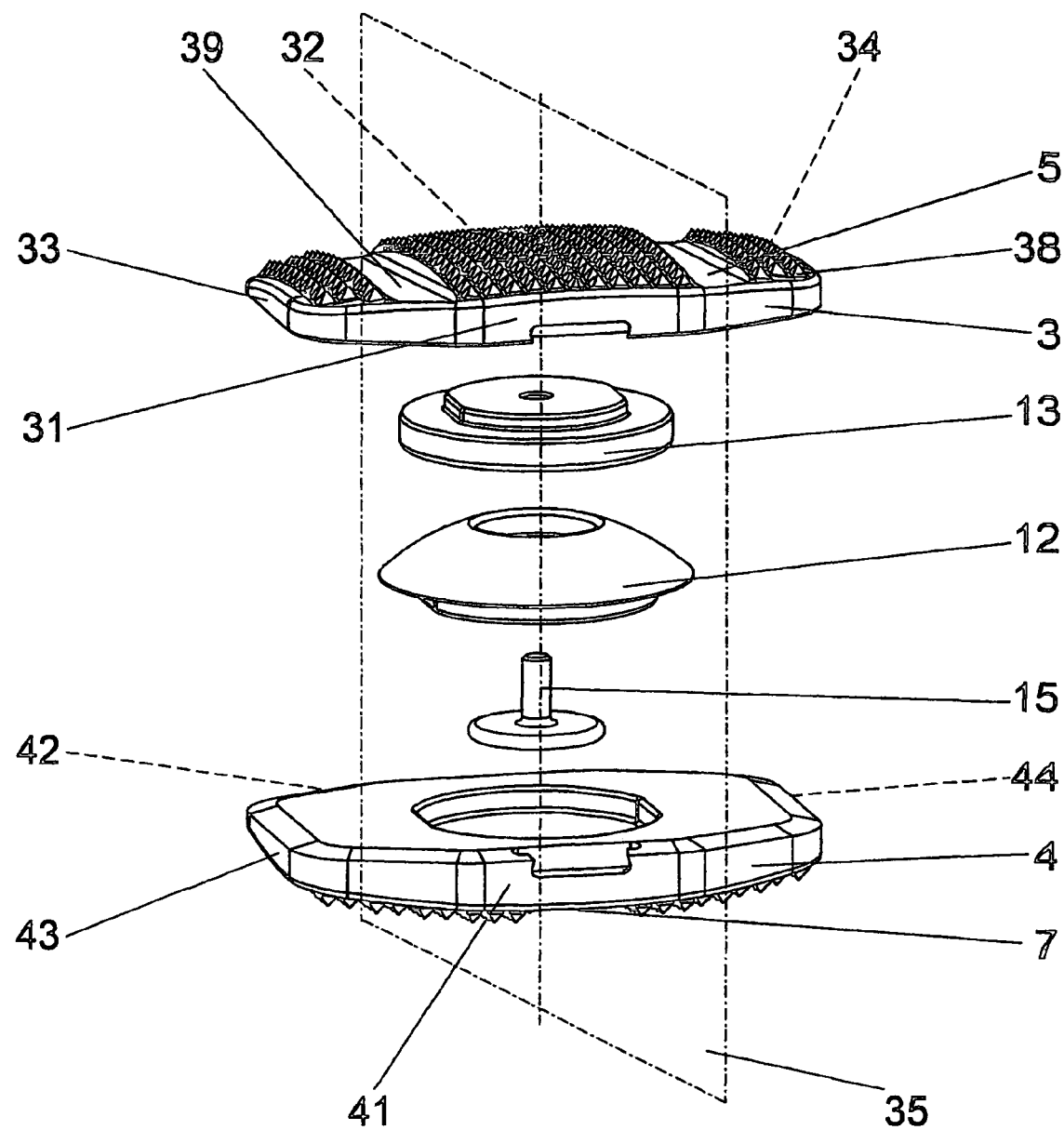
FIG. 4 is an exploded view of the device of FIGS. 1, 2 and 3.

As it is shown in FIG. 4, the top part 3 comprises a ventral side surface 31, a dorsal side surface 32, a first top lateral side surface 33 and a second top lateral side surfaces 34. The bottom part 4 comprises a ventral side surface 41, a dorsal side surface 42, a first bottom lateral side surface 43 and a second bottom lateral side surfaces 44.

Furthermore, the top apposed surface 5 and the bottom apposed surface 7 have a convex construction and are provided with protuberances 18. Between the top lateral side surfaces 33, 34 and between the bottom lateral side surfaces 43, 44 there is a central plane 35, that in this case forms also the plane of symmetry for the intervertebral implant 1. Furthermore, the top and bottom apposed surfaces 5, 7 include two parallel grooves 39, which are approximately symmetrical about the central plane 35 and terminate at least in the ventral side surfaces 31, 41 and are suitable to accommodate, for example, the arms of a tractioning instrument (not illustrated). In this case the protuberances 18 are constructed as pyramid-like protuberances 38. In one embodiment the pyramid-shaped protuberances have a volume between about 0.12 mm$^3$ and about 1.4 mm$^3$. In a further embodiment convex construction of the top and bottom apposed surfaces 5, 7 are adapted to suit the natural cover and base surfaces, respectively, of the adjacent bodies of the vertebra.

Figure 5:
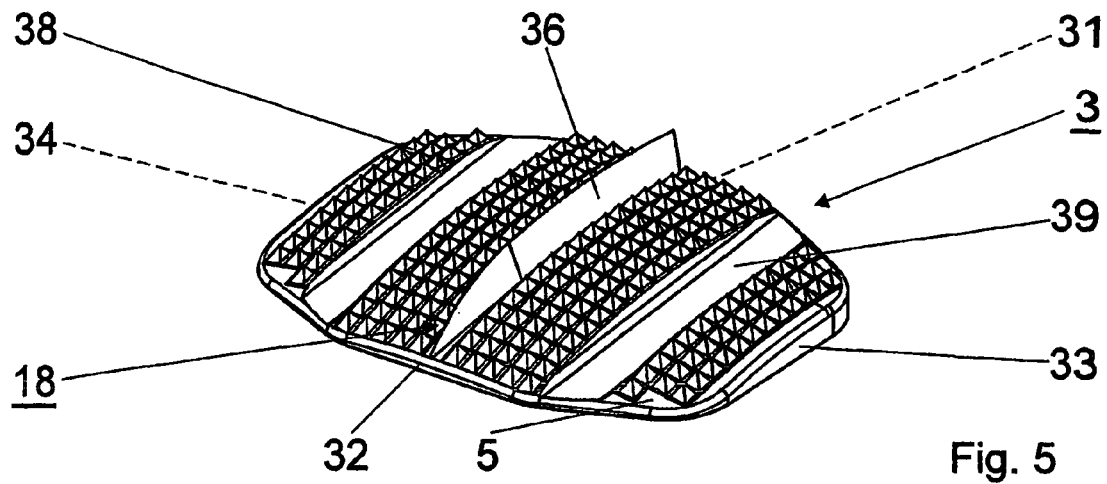
FIG. 5 is a perspective view of the top part of an alternative embodiment of the device.
Figure 6:
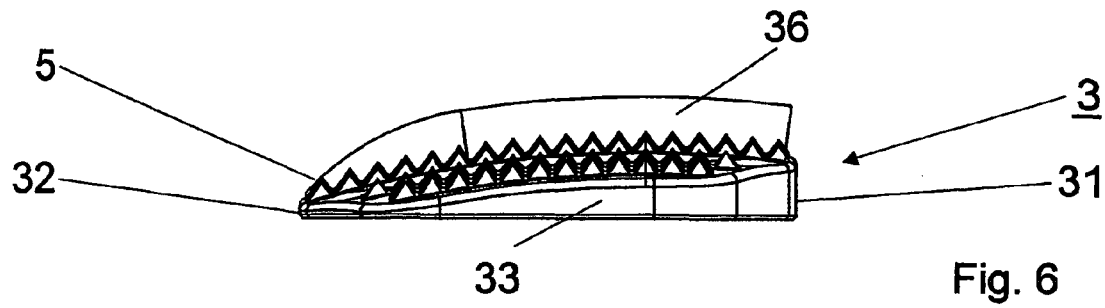
FIG. 6 is a lateral view of the top part of the embodiment of the device of FIG. 5.

In addition to the pyramid-like protuberances 38 illustrated in FIG. 4, the protuberances 18, as illustrated in FIGS. 5 and 6, may comprise a wedge-shaped rib 36 on each of the top and bottom apposed surfaces 5, 7. The wedge-shaped rib 36 is approximately symmetrical about the central plane 35. The ribs are taller than the pyramid-like protuberances 38 and are situated on the top and bottom apposed surface 5, 7 and are substantially parallel to the central plane 35 (FIG. 4). So that the intervertebral implant 1 could be more easier introduced into the intervertebral space, the height of the ribs 36 generally decreases towards the dorsal side surface 32.

Figure 7:
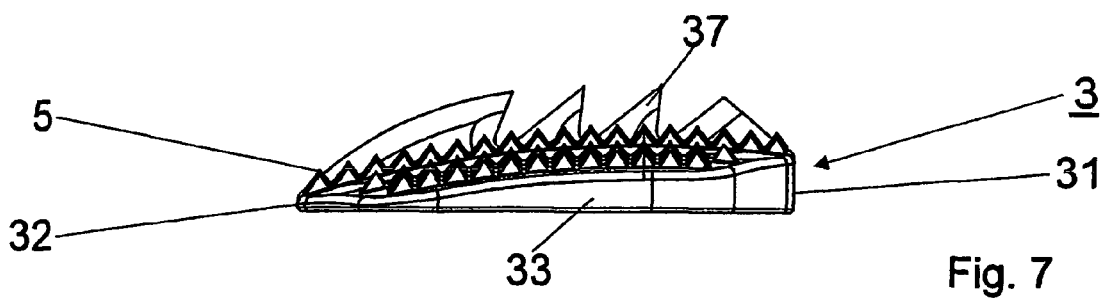
FIG. 7 is a lateral view of the top part of a further embodiment of the device.
Figure 8:
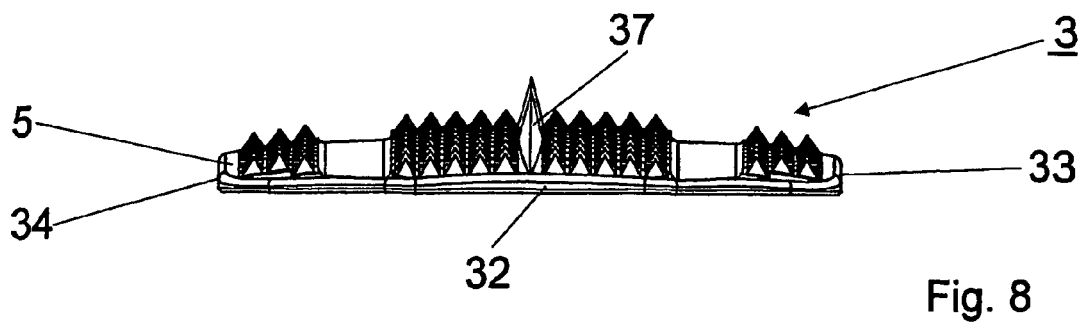
FIG. 8 is a dorsal view of the top part of the device of FIG. 7.

A further embodiment of protuberances 18 is illustrated in FIGS. 7 and 8. The serrations 37, which are taller than the pyramid-shaped protuberances 38, are constructed partly with saw-tooth shapes, while the steeper flank is facing the ventral lateral surface 31. In this case the serrations 37 are situated substantially parallel to the central plane 35 (FIG. 4) and extend from the ventral lateral surface 31 up to the dorsal lateral surface 32. In another embodiment the saw-tooth serrations 37 are arranged approximately symmetrically about the central plane 35. The advantage of the serrations is, that they can more easily penetrate into the end plates of the adjacent bodies of the vertebra.

In FIGS. 5 to 8 only the top part 3 is illustrated in the form of an example. The same construction of the protuberances 18 with pyramid-shaped protuberances 38, a rib 36 (FIGS. 5 and 6) or serrations 37 (FIGS. 7 and 8) can be applied in an analogous manner to the bottom part 4.

By virtue of these macroscopic structures (FIGS. 5-8) the advantages achievable are, that on the one hand, torques about an axis of rotation, intersecting the apposed surfaces, can be better transferred from the bodies of the vertebra to the intervertebral implant, and on the other hand the surface area, to which the bones can adhere, is increased.

In another preferred embodiment the protuberances are coated at least partially with a substance that fully integrates with bone or may even be replace with new, natural bone tissue. Examples of such substance include hydroxylapatite and bi-phased hydroxylapatite-tricalcium phosphate mixtures.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being indicated by the appended claims, and not limited to the foregoing description.

What is claimed is:

1. An intervertebral implant comprising:
   a top part having a top apposed surface for contacting an upper vertebra;
   a bottom part having a bottom apposed surface for contacting a lower vertebra;
   a convex joint part having a first articular surface, the convex joint part operatively coupled to one of the top and bottom parts; and
   a joint shell having a second articular surface, the joint shell operatively coupled to the other of the top and bottom parts,
   wherein the first and second articular surfaces are coated with an amorphous diamond-like carbon (ADLC) coating, the ADLC coating on the second articular surface of the joint shell slidably contacting the ADLC coating on the first articular surface of the convex joint part such that the top part is articulatable with respect to the bottom part about at least one axis of rotation; and
   wherein the top and bottom parts are manufactured from a metal and the convex joint part and the joint shell are manufactured from a plastic;
   wherein the convex joint part includes an inner hollow space, the implant further comprising an anchoring element including a disc-shaped extension located in the hollow space and a pin connected to the extension and passing through the joint part, through the joint shell and into engagement with one of the top and bottom parts so that the top part, the bottom part, the convex joint part and the joint shell are held together during implantation, the anchoring element enabling the joint shell and the joint part to be separatable by an axial clearance;
   wherein the pin passes through the first articular surface and the ADLC coating thereon and through the second articular surface and the ADLC coating thereon, and wherein the axial clearance is sufficiently large to allow sliding articulation between the ADLC coating on the first articular surface, the ADLC coating on the second articular surface and formation of a lubricating film therebetween.

2. The intervertebral implant of claim 1, wherein the hollow space is substantially cylindrical and coaxial with the axis of rotation.

3. The intervertebral implant of claim 2, wherein the hollow space has a diameter between about 6 mm and about 20 mm.

4. The intervertebral implant of claim 3, wherein the cylindrical hollow space has a height between about 0.5 mm and about 8 mm.

5. The intervertebral implant of claim 1, wherein the hollow space has a contraction that is coaxial with the axis of rotation and which terminates in the first articular surface of the convex joint part.

6. The intervertebral implant of claim 5, wherein the contraction is substantially cylindrical.

7. The intervertebral implant of claim 6, wherein the ratio of the diameter of the contraction to the ratio of the diameter of an uncontracted segment of the hollow space is between about 30% and about 75%.

8. The intervertebral implant of claim 6, wherein the diameter of the contraction and the diameter of the hollow space is sufficiently large to enable lateral movement of the pin during articulation.

9. The intervertebral implant of claim 1, wherein the diameter of the disc shaped extension is greater than the diameter of at least a portion of the inner hollow space.

* * * * *